United States Patent [19]

Bolg et al.

[11] Patent Number: 4,721,107
[45] Date of Patent: Jan. 26, 1988

[54] INSTRUMENT FOR ULTRASONIC LITHOTRIPSY

[75] Inventors: Ulrich Bolg, Sulzfeld; Werner Krauss, Maulbronn; Helmut Wurster, Oberderdingen, all of Fed. Rep. of Germany

[73] Assignee: Richard Wolf GmbH, Fed. Rep. of Germany

[21] Appl. No.: 870,784

[22] Filed: Jun. 5, 1986

[30] Foreign Application Priority Data

Jun. 5, 1985 [DE] Fed. Rep. of Germany ....... 3520133

[51] Int. Cl.⁴ .............................................. A61B 17/22
[52] U.S. Cl. .................................. 128/328; 128/24 A
[58] Field of Search ...................... 128/328, 24 A, 305; 604/22

[56] References Cited

U.S. PATENT DOCUMENTS 3,792,701  2/1974  Kloz et al. ........................ 128/328
4,561,438  12/1985  Bonnet et al. ...................... 128/328
4,589,415  5/1986  Haaga .............................. 128/328

Primary Examiner—Michael H. Thaler
Attorney, Agent, or Firm—Hill, Van Santen, Steadman & Simpson

[57] ABSTRACT

An instrument for ultrasonics lithotripsy comprises a probe which is applied to the stone which is to be disintegrated, which may be placed in oscillation by means of a piezo-electric sound transducer which is assembled from ceramic discs. The transducer is energized into oscillation by an electrical generator and the transducer oscillations are transmitted to the probe via a distal transducer closure. A particularly effective operation of the instrument is the result if the transducer is energized only intermittently by pulsed operation of the generator, no specific natural resonance frequencies of the system being intended to occur within the preset range of operating frequency.

6 Claims, 8 Drawing Figures

INSTRUMENT FOR ULTRASONIC LITHOTRIPSY

BACKGROUND OF THE INVENTION

The invention relates to an instrument for ultrasonic lithotripsy, comprises a probe for application to a stone which is to be disintegrated, which probe may be made to oscillate by means of a piezo-electric converter or transducer, the transducer is assembled from ceramics discs and is induced to oscillate by an electrical generator and the transducer oscillations are transmitted to the probe via a distal transducer end member.

DESCRIPTION OF THE PRIOR ART

In the case of known instruments of this nature (for example German patent specifications Nos. 20 20 345 and 20 53 982) which are applied in particular to disintegrate bladder and kidney stones by means of ultrasonic waves, the sonic transducer is operated by means of a constant signal. It has been found in practice that this procedure requires quite a long period for treatment of the stone which is to be destroyed and this period may primarily be ascribed to the comparatively small deflection of the probe.

Furthermore, the transducer systems substantially transmit only longitudinal or transverse oscillations to the probe or sonotrode, which results in a state of reentry oscillation after a brief period, which commonly leads only to a perforation and not to a break-up of the stone being treated or of parts of the stone.

SUMMARY OF THE INVENTION

It is an object of the invention to provide an instrument for ultrasonic lithotripsy which is optimised regarding the output of the transducer and generator systems as compared to the instruments known until now, and achieves a substantially faster disintegration of bodily stones.

An instrument for ultrasonic lithotripsy is so constructed according to the invention that the transducer may be energised intermittently by pulsed operation of the generator, and lacks any specific intrinsic resonance frequency within the preset range of operating frequency.

Thanks to the intermittent or rather pulsed energisation of the transducer and the consequently also intermittent operation of the probe, it is possible to operate the transducer with a high output without the risk of overloading and thereby to secure correspondingly large oscillation amplitudes at the probe extremity. Furthermore, mechanical oscillation build-up and decay actions will occur at the probe at the onset and termination of each electrical pulse fed to the transducer thanks to this intermittent mode of operation, which will have the result that the probe does not preponderantly "drill" into the stone but causes the stone to burst, primarily by causing transverse deflections of different amplitude.

Compared to an electrohydraulic wave surge lithotripsy in which it is also possible if necessary to transmit single hydraulic pulses to the stone situated at a distance from the distal probe extremity, the ultrasonic lithotripsy is generally less risky as well as easier to apply, and more effective moreover in numerous cases using the instrument according to the invention.

The ceramic disc structure of the transducer is delimited by proximal and a distal transducer end members or closures. To this end, the transducer may be closed off reflectionlessly at the proximal end, at least to a substantial degree, by means of the impedance of its ceramic discs, the mass of the distal transducer closure being intended to be smaller than the mass of the proximal transducer closure, in this case. As for the rest, to secure a reflectionless closure, it is appropriate for the free end surface of the proximal transducer closure to have an irregular outline and thus to form a diffuse termination for the sound wave coming from the transducer.

The proximal transducer closure may however also be so formed and dimensioned that it reflects the sound waves to an optimum degree, in which case the free end surface of the proximal transducer delimitation should be plane and parallel to the plane of the ceramic discs of the transducer.

Moreover, the generator supplying the transducer with electrical energising pulses comprises at least one capacitor chargeable with direct current, which may in each case be discharged in pulsed manner via the transducer by means of at least one triggered spark gap. To this end, two triggered spark gaps and two capacitors may form separate circuits, so that the capacitors may be switched to the transducer successively by firing of the associated spark gap, whereas the other capacitor is being recharged whilst the first is being discharged, so that a continuous pulse sequence may be obtained.

Another possibility for the construction of the generator consists in connecting four spark gaps and two trigger generators in such manner that two spark gaps are energised in each case consecutively by means of the one trigger generator, and that positive and negative pulses are thereby supplied to the transducer alternately.

Finally, the transducer comprising its ceramic discs, the distal transducer end member carrying the probe, and the proximal transducer end member may be releasably connected by means of a stressing element whereas the overall structure or rather the transducer, should be so designed that no specific natural resonance frequencies occur in the preset range of operating frequency and that the transducer rapidly follows the imposed electric voltage.

Some examples of embodiment of the invention which are described in particular in the following, are illustrated diagrammatically in the accompanying drawings.

DETAILED DESCRIPTION OF THE PREFERRED EMBODIMENTS

Figure 1:
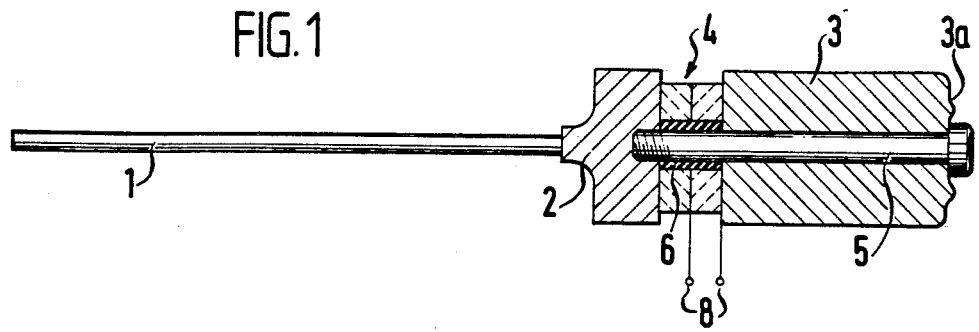
FIGS. 1 to 4 are partial longitudinal cross sectional view with portions in elevation of different instruments according to the present invention.

The embodiments shown in FIGS. 1 to 4 are substantially analogous in fundamental structure, so that the same reference symbols are used in each case for identical or functionally analogous or equivalent components, to simplify the description. The instruments comprise a probe 1 which is rigidly fastened to a distal transducer closure 2. The piezo-electric transducer 4 which is formed by at least one pair of ceramic discs is in each case clamped between the closure 2 and the proximal transducer closure 3, that is to say in the case of FIGS. 1 to 3 by means of a bolt 5 which is inserted through central holes of the transducer closure 3 and of the transducer 4 and is screwed into the transducer closure 2.

In the region of the transducer 4, the bolt 5 is encircled by a resilient sleeve 6 of insulating material, so that the pairs of ceramic discs are not electrically short-circuited. The same result is logically achieved by the sleeve 6 in the instrument according to FIG. 4, in which a bolt is replaced by a clamping element 7 in the form of a cap nut which receives the distal transducer closure 2 and the ceramic discs of the transducer 4 and clamps these parts by being screwed onto the proximal transducer closure 3.

The structure and function of the piezo-electric transducer are known and consequently need not be described in detail. As for the rest, the transducer 4 is supplied in pulsed manner via connections 8 with current from the electrical generator described in the following, to which end the ceramics disc pairs (FIG. 3) extend parallel to the connections 8 if several such pairs are utilised.

In the case of the instrument according to FIG. 1, the transducer 4 is delimited in reflectionless manner with, at least substantially, the impedance of the ceramics discs pair forming the transducer. Accordingly, the mass of the distal transducer closure 2 is smaller than the mass of the proximal transducer closure, whereby different natural resonances are generated at the distal and proximal transducer closures. To secure a reflectionless termination, the material and the longitudinal dimensions of the two transducer closures also have to be organised accordingly, whereas the free end surface 3a of the proximal transducer closure 3 is irregularly contoured in accordance with the illustration and will consequently cause a diffuse reflection. In this embodiment no sound waves, or at most a negligible proportion of sound waves of the energising signal coming from the transducer 4 are reflected at the end surface 3a, so that the probe is fundamentally induced to generate a positive surge only.

Figure 2:
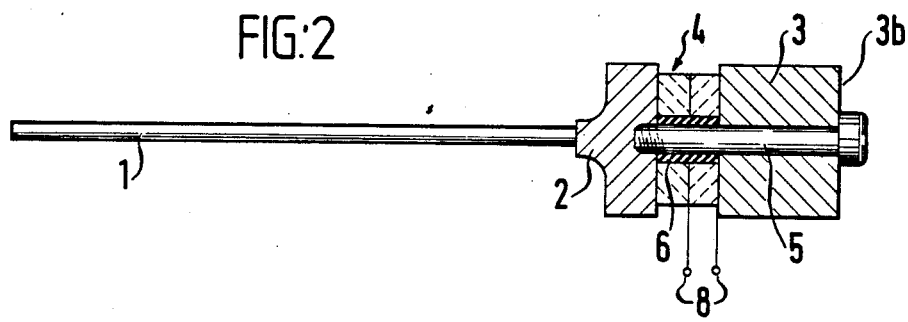

According to FIG. 2, another possibility consists in dispensing with a reflectionless termination for the ultrasonics transducer 4, but in operating the same with a reflective closure 3, so that positive sound wave pulses are reflected at the free end surface 3b under phase reversal so that negative pressure pulses having a very steep rise gradient also occur at the extremity of the probe 1. Cavitation bubbles of high energy content, which complementarily enhance the bursting action on the stone, concomitantly occur on the stone being treated. Furthermore, the plane end surface 3b of the closure 3 should extend parallel to the plane of the ceramic discs of the transducer 4 in this case to secure an optimum reflective action.

Figure 3:
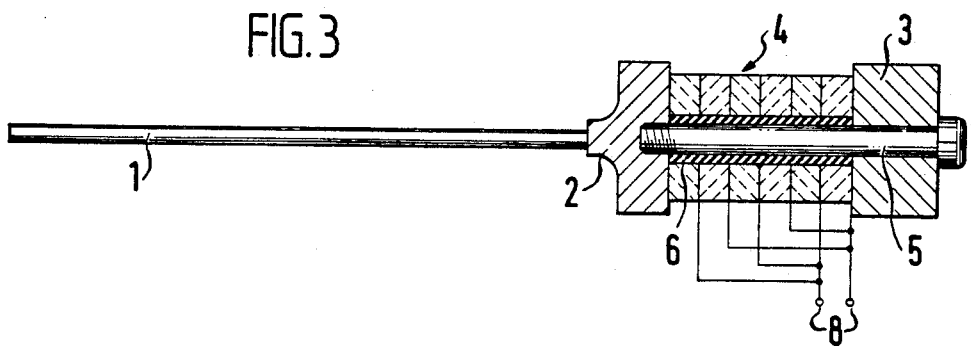
Figure 4:
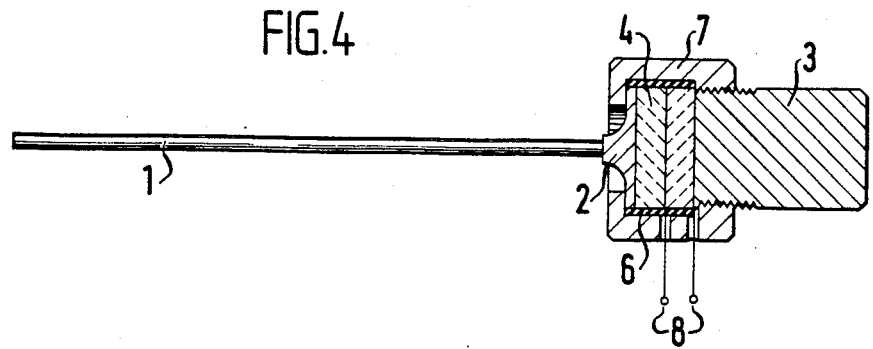

The transducer 4 may also be assembled from more than one pair of ceramic discs. FIG. 3 shows a transducer comprising three pairs of discs, which can offer a substantially greater output as compared to the transducers according to FIGS. 1, 2 and 4. If it is intended moreover to obtain brief rise times of the ultrasonic signal and thus a rapid deflection or rather longitudinal variation of the probe 1, the masses of the two transducer closures 2, 3 should logically be selected as small as possible.

FIGS. 5 to 8 show electrical generators which are particularly appropriate for operating the transducers of the instruments described in the foregoing. These generators comprise at least one capacitor charged with direct current, which is discharged in pulsed form in each case via the transducer by means of at least one triggered spark gap and is subsequently recharged automatically from a d.c. source.

Figure 5:
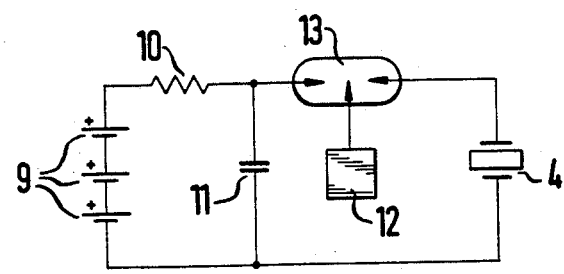
FIGS. 5 to 8 show several possible circuits for the electrical generator.

The generator according to FIG. 5 is an uncomplicated embodiment as regards circuitry, wherein the d.c. source or battery 9 charges the said capacitor 11 via a biassing resistor 10. A trigger generator 12 fires the spark gap 13 if need be, so that the energy of the charge of the capacitor is delivered to the sound transducer 4 in pulsed form.

Figure 6:
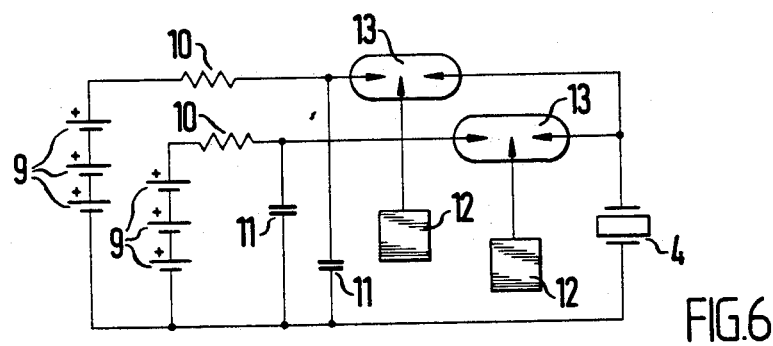

So that two voltage pulses may be transmitted to the sound transducer with a brief interval between them by means of the generator, the circuit diagram shown in FIG. 5 need merely be twinned, so that the inherently understandable circuit according to FIG. 6 then forms the result. In this case, two triggered spark gaps and two capacitors form separate circuits, the capacitors being liable to be switched to the transducer consecutively by the firing of the spark gaps.

Figure 7:
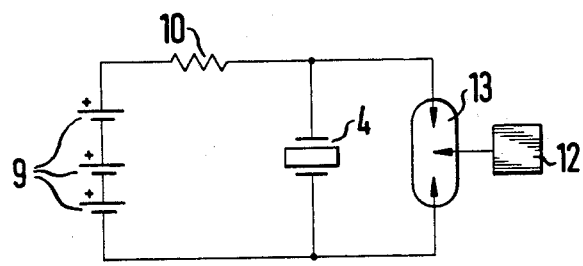

By contrast to the two examples of circuits described earlier, the transducer 4 itself is utilised as a capacitor according to FIG. 7. In this case, the battery 9 thus charges the transducer 4 via the resistor 10. The trigger generator 12 may be fired via the spark gap 13, thereby short-circuiting the transducer which is discharged violently, causing a negative surge at the probe.

Figure 8:
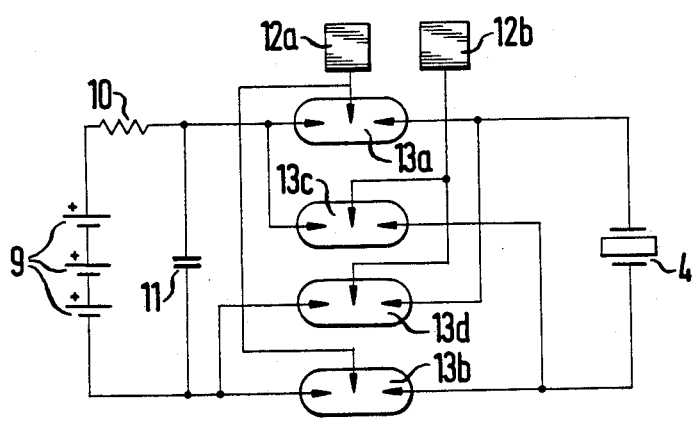

FIG. 8 finally shows a generator in which four spark gaps and two trigger generators are so connected that two spark gaps 13a, 13b may be energized in each case by means of a trigger generator 12a, and that the two other spark gaps 13c, 13d may be energised by means of the other trigger generator 12b. In this connnection, the transducer 4 may consequently also be supplied with single positive or negative current pulses or else alternately with negative and positive current pulses, which obviously presupposes a commensurate adjustability and controllability of the two trigger generators.

In a manner known per se, the probe 1 may comprise a tube or a thin flexible wire. On the other hand, the probe may also be formed by several steel wires which are twisted together and coated with plastics material, the coating being intended to prevent a sonic loss between the wires.

What is claimed is:

1. An instrument for ultrasonic lithotripsy by applying oscillations from a probe to a stone to be disintegrated, said instrument comprising a piezo-electric transducer including at least a pair of ceramic discs arranged between a proximal end member and a distal end member, an electric generator for energizing said transducer with a pulse operation and a probe extending from said distal end member, said distal end member having a mass less than the mass of the proximal end member and the disc having an impedance selected so that said transducer will have no specific natural resonance frequency in the preset range of operating frequencies and will be substantially reflection-free at the proximal end member.

2. An instrument as claimed in claim 1, wherein said electrical generator has at least one capacitor chargeable by means of direct current, arranged in each case to be discharged in pulsed manner via the transducer with at least one triggered spark gap.

3. An instrument as claimed in claim 2, wherein at least two triggered spark gaps and at least two capacitors form separate circuits and wherein the capacitors are switchable one after another by firing of the associated spark gaps, to the transducer.

4. An instrument as claimed in claim 2, wherein at least two spark gaps and two trigger generators are so connected that at least two spark gaps are energizable one after another by means of one of the trigger generators to enable positive and negative pulses to be fed alternately to the transducer.

5. An instrument as claimed in claim 1, wherein the transducer itself is utilised as a capacitor and is discharged across a spark gap.

6. In an instrument according to claim 1, wherein the proximal end member has a free end surface with an irregular and difusably reflecting profile.

* * * * *